(12) United States Patent
Ruiz Gallardo

(10) Patent No.: US 11,480,113 B2
(45) Date of Patent: Oct. 25, 2022

(54) METHOD AND A SYSTEM FOR CHARACTERIZING THE FUEL ON BOARD AN AIRCRAFT

(71) Applicant: Airbus Operations (S.A.S.), Toulouse (FR)

(72) Inventor: Alvaro Ruiz Gallardo, Toulouse (FR)

(73) Assignee: Airbus Operations (S.A.S.), Toulouse (FR)

( * ) Notice: Subject to any disclaimer, the term of this patent is extended or adjusted under 35 U.S.C. 154(b) by 297 days.

(21) Appl. No.: 16/428,283

(22) Filed: May 31, 2019

(65) Prior Publication Data

US 2019/0376453 A1    Dec. 12, 2019

(30) Foreign Application Priority Data

Jun. 7, 2018   (FR) ...................................... 1854951

(51) Int. Cl.
*F02C 9/52*   (2006.01)
*F02C 7/22*   (2006.01)
*B64D 37/00*  (2006.01)

(52) U.S. Cl.
CPC .................. *F02C 9/52* (2013.01); *F02C 7/22* (2013.01); *B64D 37/00* (2013.01); *F05D 2270/20* (2013.01)

(58) Field of Classification Search
CPC .. F02C 9/52; F02C 7/22; B64D 37/14; G01N 33/2852
See application file for complete search history.

(56) References Cited

U.S. PATENT DOCUMENTS

| | | |
|---|---|---|
| 2009/0319153 A1 | 12/2009 | Bradley et al. |
| 2012/0260731 A1* | 10/2012 | Austerlitz ............ B64D 37/005 |
| | | 73/32 R |
| 2013/0257457 A1* | 10/2013 | Kato ...................... G01N 27/22 |
| | | 324/663 |

(Continued)

FOREIGN PATENT DOCUMENTS

| | | |
|---|---|---|
| EP | 2 330 393 A1 | 6/2011 |
| EP | 3 220 175 A1 | 9/2017 |

(Continued)

OTHER PUBLICATIONS

French Search Report for Application No. 1854951 dated Mar. 28, 2019.

*Primary Examiner* — Eric S. McCall
*Assistant Examiner* — Timothy P Graves
(74) *Attorney, Agent, or Firm* — Jenkins, Wilson, Taylor & Hunt, P.A.

(57) ABSTRACT

A method and system for acquiring fuel characteristics on board an aircraft. The method for acquiring fuel characteristic on board an aircraft includes a least one tank and comprises a determination step determining a fuel circuit in one tank among the tank or tanks. The circuit includes at least one pump pumping the fuel from the tank into the circuit. A fuel properties measurement unit and a first valve are configured to open or close the circuit. A filling step includes filling the circuit with fuel. An acquisition step includes acquiring a value respectively for each of the fuel characteristics of the tank, and a transmission step includes transmitting, to a user device, a signal representative of the acquired values of the fuel characteristics.

12 Claims, 3 Drawing Sheets

(56) References Cited

U.S. PATENT DOCUMENTS

| | | | |
|---|---|---|---|
| 2015/0217153 A1* | 8/2015 | Jones | B64D 45/00 |
| | | | 169/62 |
| 2016/0169112 A1* | 6/2016 | Morioka | F02C 7/236 |
| | | | 60/735 |
| 2017/0320587 A1* | 11/2017 | Dumas | F04B 43/04 |

FOREIGN PATENT DOCUMENTS

| | | |
|---|---|---|
| WO | WO 2013/116799 A1 | 8/2013 |
| WO | WO 2016/046485 A1 | 3/2016 |

* cited by examiner

METHOD AND A SYSTEM FOR CHARACTERIZING THE FUEL ON BOARD AN AIRCRAFT

CROSS-REFERENCE TO RELATED APPLICATION

This application claims priority to French patent application number 18 54951 filed on Jun. 7, 2018, the entire disclosure of which is incorporated by reference herein.

TECHNICAL FIELD

The disclosure herein relates to a method and a system for characterizing the fuel on board an aircraft.

BACKGROUND

Although not exclusively, the disclosure herein applies to an aircraft, more particularly a transport aircraft, which includes a plurality of fuel tanks arranged in the wings and in the fuselage.

The determination of the fuel on board an aircraft relies, generally, on measurements of the characteristics of the fuel, in particular the density, the permittivity and the temperature of the fuel, by a Fuel Properties Measurement Unit or FPMU, arranged in each tank of the aircraft. This operation takes place on the ground when refuelling the aircraft, that is to say when filling the central tank and the wing tanks of the aircraft with fuel. The acquisition of such data by the fuel properties measurement unit and the parameters specific to the tanks of the refuelled aircraft make it possible to determine the mass of fuel in each of the tanks of the aircraft. The mass of fuel is then converted into information about the quantity of fuel present in each tank of the aircraft. This information can be displayed on a screen of the crew instrument panel or used by a flight control unit.

As a general rule, the FPMU measures the fuel characteristics when it has been full for a time long enough to provide precise measurements of the fuel characteristics. Now, there are situations when the FPMU is not sufficiently filled with fuel to allow precise measurements of the fuel characteristics. There are other situations when the FPMU is sufficiently filled but for times too short to allow precise measurements. For example, if the flow rate of fuel supplied by a tanker when filling a tank is below a certain threshold, or if the flow rate of fuel varies over time such that it passes below this threshold, the FPMU is not filled with fuel for a time long enough to measure precisely the fuel characteristics.

In such situations, the solution consists of or comprises emptying then refilling the tank of the aircraft so as to start again the process of measuring the fuel characteristics using the fuel properties measurement unit. This common solution causes a significant loss of time in refuelling the aircraft.

The aim of the disclosure herein is to remedy these disadvantages.

SUMMARY

The disclosure herein relates to a method for acquiring fuel characteristics on board an aircraft, the aircraft comprising at least one tank.

According to the disclosure herein, the method for acquiring fuel characteristics comprises the succession of following steps:

a circuit determination step, implemented by a determination unit, the determination step consisting of or comprising determining a fuel circuit in one tank among the tank or tanks, circuit intended for circulating the fuel, the fuel circuit comprising at least one pump configured to pump the fuel from the tank into the circuit, a fuel properties measurement unit and a first valve configured to open or close the fuel circuit;

a filling step, implemented by a filling unit, the filling step consisting of or comprising filling with fuel the circuit determined at the circuit determination step, the fuel being pumped into the circuit by the pump of the tank until inside the fuel properties measurement unit, and consisting of or comprising blocking the fuel in the fuel properties measurement unit by closing the first valve;

an acquisition step of the fuel characteristics in the tank, implemented by an acquisition unit, the acquisition step consisting of or comprising acquiring a value, measured by the fuel properties measurement unit, respectively for each of the fuel characteristics of the tank; and a transmission step, implemented by a transmission unit, consisting of or comprising transmitting, to a user device, a signal representative of the acquired values of the fuel characteristics.

Thus, thanks to the disclosure herein, the acquisition of values of the fuel characteristics is ensured by the fuel properties measurement unit, which is filled directly with fuel from one of the tanks of the aircraft. This makes it possible to eliminate the risks of fuel flow rate variation in connection with refuelling the tanks of the aircraft, which could necessitate emptying then refilling the tank or tanks of the aircraft.

Advantageously, the fuel characteristics comprise at least:
a density;
a temperature; and
a permittivity.

Furthermore, the method for acquiring fuel characteristics also comprises a selection step of a tank among the fuel tank or tanks of the aircraft, implemented by a selection unit, upstream of the circuit determination step, the selection step consisting of or comprising selecting a tank containing fuel.

The method for acquiring fuel characteristics preferably also comprises a bleed step of the circuit, between the circuit determination step and the filling step, the bleed step of the circuit being implemented by a bleed unit and consisting of or comprising controlling the bleeding of the fuel circuit for a predetermined bleed time, by opening the first valve.

Furthermore, the method for acquiring fuel characteristics comprises an emptying step of the fuel circuit, implemented by an emptying unit, downstream of the transmission step, the emptying step consisting of or comprising stopping pumping the fuel into the circuit through the pump and emptying the fuel from the circuit by opening a passive mechanical valve of the circuit.

In a preferred embodiment, the acquisition step comprises a convergence sub-step, implemented by a convergence module, consisting of or comprising acquiring a succession of auxiliary values, measured during a predetermined acquisition time by the fuel properties measurement unit, of each characteristic of the fuel, the succession of auxiliary values of each characteristic of the fuel converging during the acquisition time towards an acquisition value of each fuel characteristic, the acquisition value representing the value of each characteristic of the fuel transmitted to the user device.

The disclosure herein also relates to a system for acquiring fuel characteristics on board an aircraft, the aircraft being provided with at least one fuel tank.

According to the disclosure herein, the system for acquiring fuel characteristics comprises:

a determination unit configured to determine a fuel circuit in one tank among the tank or tanks, intended for circulating the fuel, the fuel circuit comprising at least one pump configured to pump the fuel from the tank into the circuit, a fuel properties measurement unit and a first valve configured to open or close the fuel circuit;

a filling unit configured to fill the circuit, determined by the determination unit, with fuel, the fuel being pumped into the circuit by the pump of the tank until inside the fuel properties measurement unit, and configured to block the fuel in the fuel properties measurement unit by closing the first valve;

an acquisition unit configured to acquire a value, measured by the fuel properties measurement unit, respectively for each of the fuel characteristics of the tank; and a transmission unit configured to transmit, to a user device, a signal representative of the acquired values of the fuel characteristics.

Advantageously, the system for acquiring fuel characteristics comprises a selection unit configured to select, among the fuel tank or tanks of the aircraft, a tank containing fuel.

Furthermore, the system for acquiring fuel characteristics comprises a bleed unit configured to control the bleeding of the fuel circuit for a predetermined bleed time, by opening the first valve.

The system for acquiring fuel characteristics preferably comprises an emptying unit configured to stop pumping the fuel into the circuit through the pump and to empty the fuel from the circuit by opening a passive mechanical valve of the circuit.

Furthermore, the fuel properties measurement unit comprises a convergence module, configured to acquire a succession of auxiliary values, measured by the fuel properties measurement unit, of each characteristic of the fuel during a predetermined acquisition time, the succession of auxiliary values of each characteristic of the fuel converging during the acquisition time towards an acquisition value of each fuel characteristic, the acquisition value representing the value of each characteristic of the fuel transmitted to the user device.

The disclosure herein furthermore comprises an aircraft, in particular a transport aircraft, which is equipped with a system for acquiring fuel characteristics as mentioned above.

BRIEF DESCRIPTION OF THE DRAWINGS

The attached figures will make how the disclosure herein can be embodied easy to understand. In these example figures, identical reference numbers designate similar elements. More particularly.

DETAILED DESCRIPTION

Figure 1:
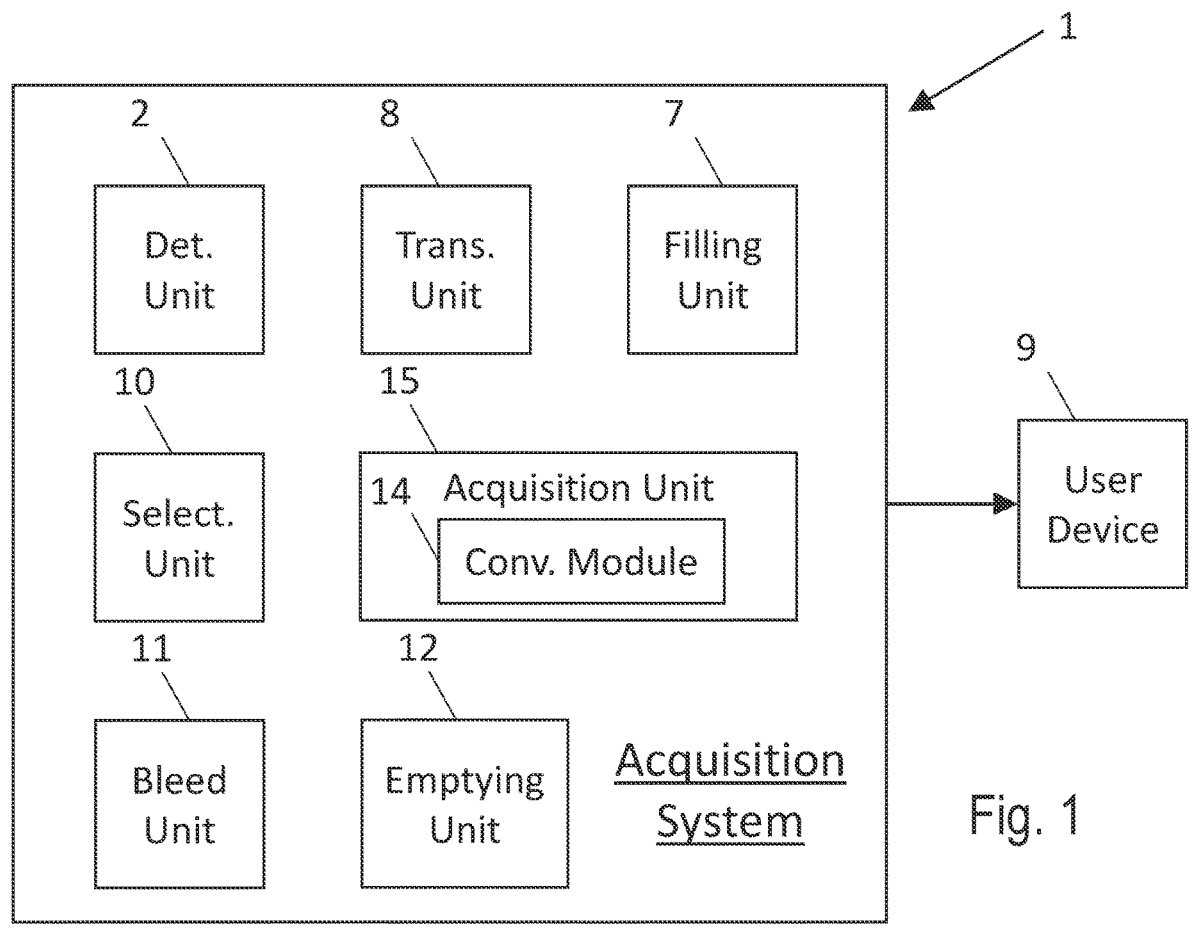
FIG. 1 is a view of an overview diagram of a system for acquiring fuel characteristics illustrating an embodiment of the disclosure herein.
Figure 2:
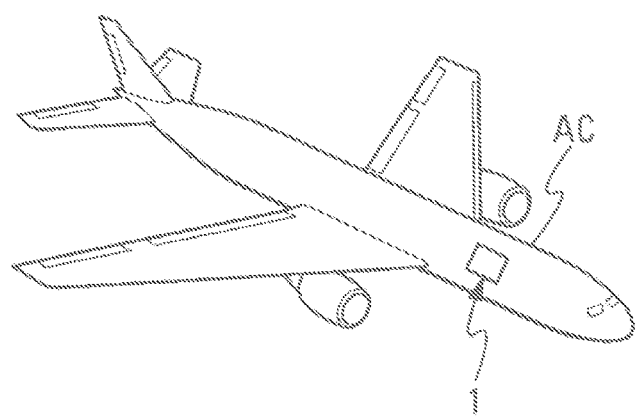
FIG. 2 diagrammatically shows in perspective an aircraft with an on board acquisition system.

The system for acquiring characteristics of fuel on board an aircraft (hereinafter "acquisition system 1"), diagrammatically shown in an embodiment in FIG. 1, is intended to acquire values of several characteristics of the fuel present in one or more tanks CT, WT1, WT2 of an aircraft AC (FIG. 2). These values of characteristics of the fuel are used in predetermined tables of calculation so as to determine the mass of the fuel that is present. The mass of the fuel is an important piece of data in terms of flight control of the aircraft AC. As an example, the mass of the fuel makes it possible to determine the centre of gravity of the aircraft AC.

Figure 4:
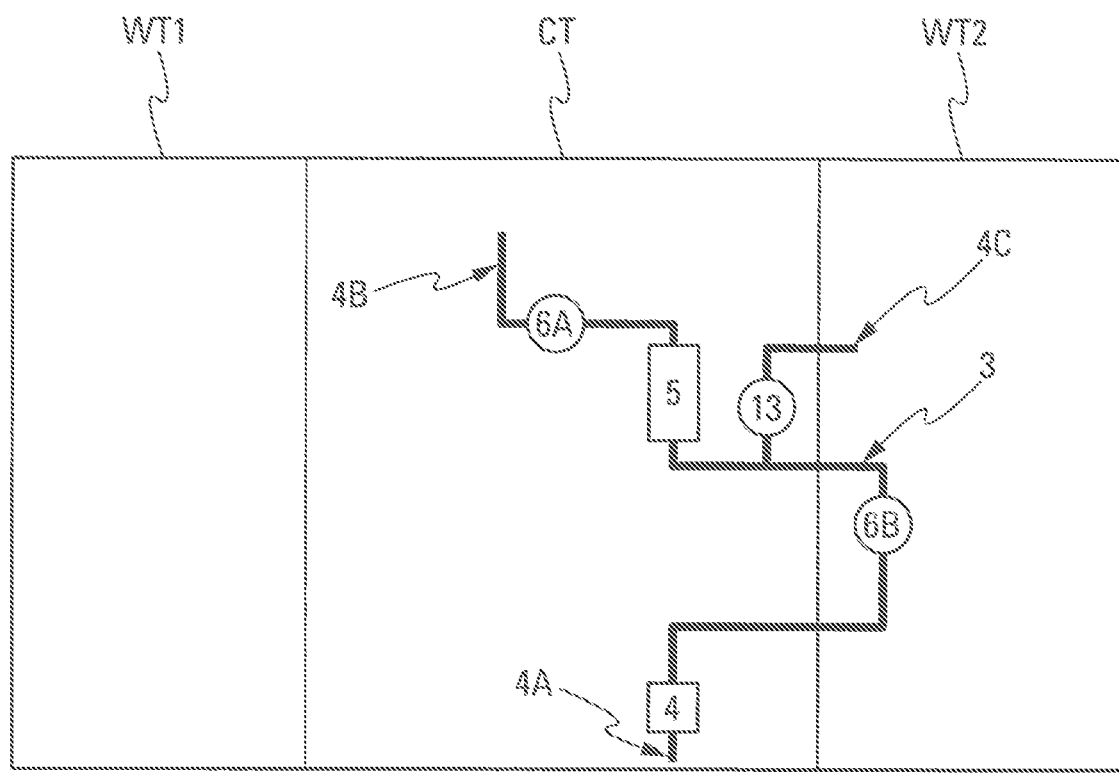
FIG. 4 diagrammatically illustrates a fuel circuit in a central tank, according to an embodiment.
Figure 5:
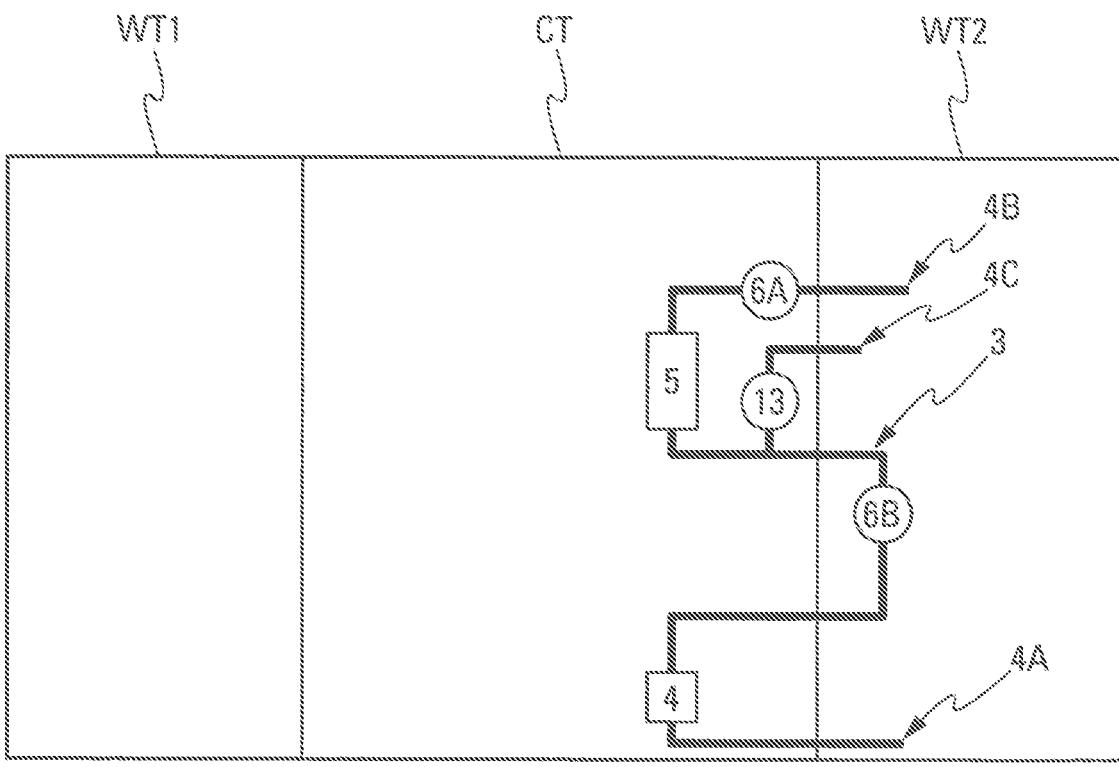
FIG. 5 diagrammatically illustrates a fuel circuit in one of the wing tanks, according to another embodiment.

The aircraft AC preferably comprises a central tank CT and two wing tanks WT1 and WT2 (FIGS. 4 and 5). Each wing tank WT1, WT2 is arranged respectively in one of the wings of the aircraft AC, either side of the central tank CT. The fuel characteristics of the central tank CT can be different from the characteristics of the wing tanks WT1 and WT2.

As shown in FIG. 1, the acquisition system 1 comprises a plurality of units.

The acquisition system 1 thus comprises a determination unit 2 configured to determine a fuel circuit 3 in one tank among the tanks CT, WT1, WT2 of the aircraft AC. As shown in FIGS. 4 and 5, the fuel circuit 3 is a succession of pipes intended for the circulation of fuel. The circuit 3 comprises a pump 4 configured to pump the fuel present in a central tank CT or one of the wing tanks WT1, WT2 and to inject it into the circuit 3. Each tank CT, WT1, WT2 preferably comprises a pump 4. According to a variant, the circuit 3 includes a single pump 4 arranged in the central tank CT. The circuit 3 comprises a first end 4A through which the fuel is injected into the circuit 3. The circuit 3 also comprises a second end 4B, opposite the end 4A and through which fuel can exit. The ends 4A and 4B of the circuit 3 can be arranged in the central tank CT, as shown in FIG. 4, or in one of the wing tanks WT1, WT2, as shown in FIG. 5. The circuit 3 also comprises a FPMU 5, configured to measure values of the fuel characteristics. For example, the FPMU 5 comprises a densitometer configured to measure the density of the fuel, a compensator configured to measure the permittivity of the fuel and a fuel temperature sensor. The density, the permittivity and the temperature of the fuel respectively represent a fuel characteristic. An aircraft AC preferably comprises at least one FPMU 5.

The circuit 3 additionally comprises a first valve 6A. The valve 6A is arranged downstream of the measurement unit 5 in the direction of circulation of the fuel in the circuit 3. The valve 6A is configured to open or close the circuit 3 of the fuel. The term "open" refers to an element allowing the circulation of the fuel or of any other type of fluid in a pipe or in the circuit 3. The term "closed" refers to an element blocking the passage of the fuel or of any other type of fluid in a pipe or in the circuit 3.

The acquisition system 1 comprises a filling unit 7 configured to fill the circuit 3 with fuel pumped by the pump 4 of the tank CT, WT1, WT2 until inside the fuel properties measurement unit 5. The filling unit 7 is also configured to close the valve 6A so as to block the fuel pumped into the circuit 3 and in particular into the fuel properties measurement unit 5.

The acquisition system 1 preferably also comprises an acquisition unit 15 configured to acquire a value respectively for each characteristic of the fuel of the tank CT, WT1, WT2.

Furthermore, the acquisition system 1 comprises a transmission unit 8 configured to transmit a signal, representative of the values of the fuel characteristics acquired by the acquisition unit 15, to a user device 9.

In a preferred embodiment, shown in FIG. 1, the acquisition system 1 also comprises a unit 10 for selecting tank CT, WT1, WT2. The selection unit 10 is configured to select, among the central tank CT and wing tanks WT1, WT2, a tank whose fuel characteristics are to be acquired. The selection unit 10 detects whether the tank CT, WT1, WT2 contains fuel and if it contains same in sufficient quantity to fill the FPMU 5. Advantageously, the central tank CT or wing tank WT1, WT2 is only selected if it contains sufficient fuel.

Furthermore, the acquisition system 1 can comprise a bleed unit 11. The bleed unit 11 is configured to control the bleeding of the circuit 3 before it is filled with fuel. The bleed unit 11 is configured to control the pump 4 and the valve 6, shown in FIGS. 4 and 5. The pump 4 is set to operate and pumps fuel into the circuit 3. The valve 6A is open during a predetermined bleed time.

In the preferred embodiment, shown in FIG. 1, the acquisition system 1 includes an acquisition unit 15, which comprises a convergence module 14. The convergence module 14 is configured to acquire a succession of auxiliary values, which are measured during a predetermined acquisition time by the FPMU 5, of each fuel characteristic of the selected tank. The succession of auxiliary values of each fuel characteristic converge, during the predetermined acquisition time, towards an acquisition value representing the value of each fuel characteristic transmitted to the user device 9.

According to a variant, the circuit 3 comprises a passive mechanical valve 13 arranged on a pipe between the valve 6A and the pump 4. The expression passive mechanical valve refers to a valve comprising a mechanical element allowing a flow to pass through the valve in a first direction but preventing the flow from passing through the valve in the direction opposite to the first direction without the intervention of an operator or a control signal. The passive mechanical valve 13 is closed when fuel circulates or is present without circulating in the circuit 3. The passive mechanical valve 13 opens in the absence of pressure in the pipes of the circuit 3. As shown in FIGS. 4 and 5, the pipe on which the passive mechanical valve 13 is arranged comprises an end 4C. This end 4C is preferably situated in a wing tank WT1, WT2.

The acquisition system 1 comprises an emptying unit 12. The emptying unit 12 is configured to control stopping the pump 4 and opening the valve 6A. In the absence of pressure in the circuit 3, the mechanical valve 13 opens. The fuel present in the circuit 3 exits through an end 4C of the mechanical valve 13.

According to a variant, the circuit 3 includes a second valve 6B arranged upstream of the measurement unit 5 in the direction of circulation of the fuel in the circuit 3, between the passive mechanical valve 13 and the pump 4. The pipes forming the part of the circuit 3 between the pump 4 and the valve 6B correspond to a part of a circuit for supplying the engines with fuel (not illustrated). The pipes forming the part of the circuit 3 between the valve 6B and the end 4B correspond to a part of a circuit for refuelling the tanks (not illustrated). When the valve 6B is closed, it is configured to prevent the circulation of fuel in the circuit for supplying the engines and to allow the fuel to circulate in the circuit 3. When the valve 6B is open, it is configured to allow the fuel to circulate in the circuit for supplying the engines and to prevent the fuel from circulating in the circuit 3. The valve 6B represents a valve for diverting fuel into the circuit 3. The filling unit 7 and the bleed unit 11 are henceforth configured to close the valve 6B when the fuel is pumped into the circuit 3 and to open the valve 6B when the pump 4 is stopped.

Figure 3:
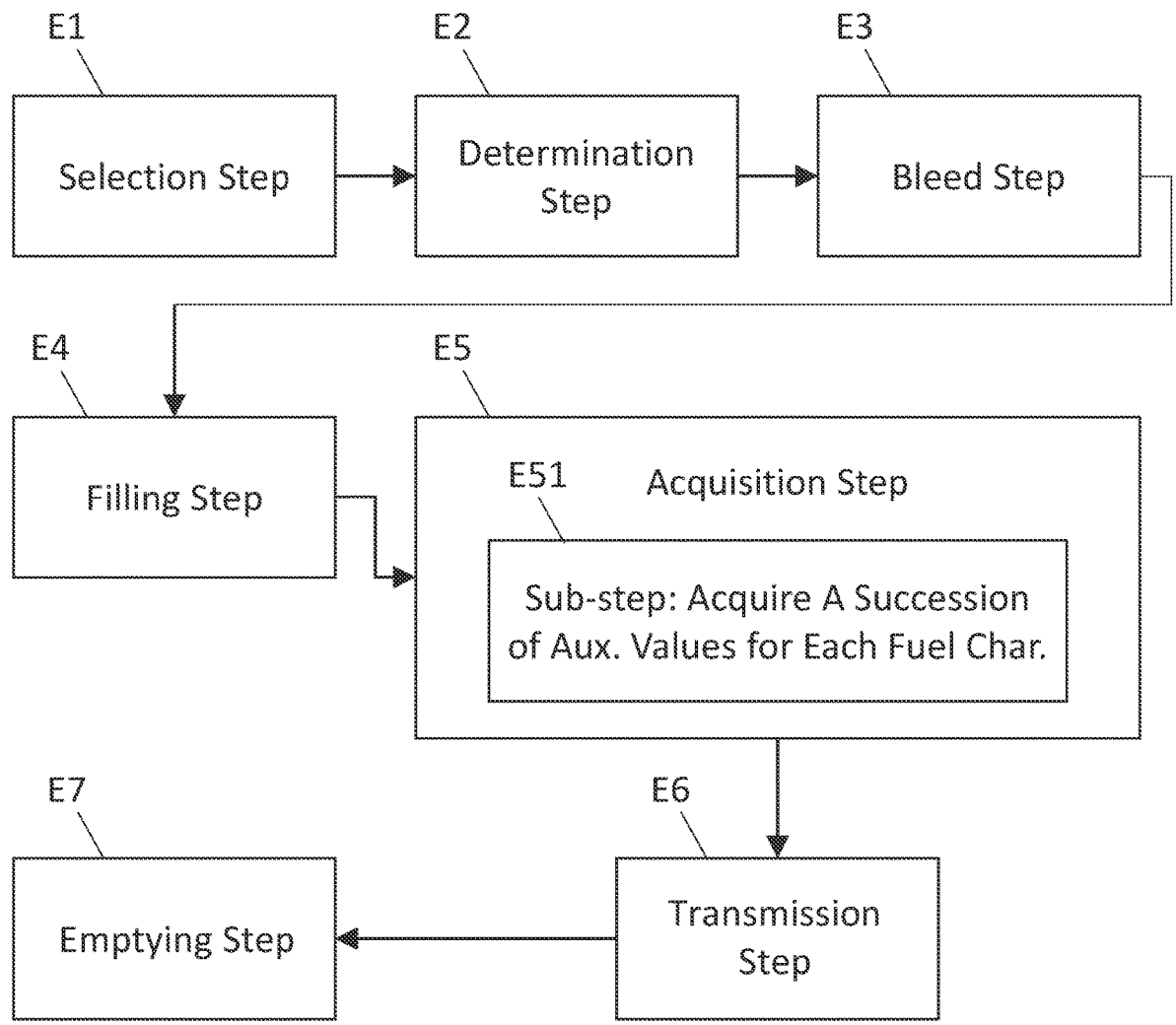
FIG. 3 diagrammatically shows an acquisition method comprising a succession of steps, according to an embodiment.

The acquisition system 1, as described above, is presented hereinafter by a method for acquiring fuel characteristics on board the aircraft AC, method shown in FIG. 3. The acquisition method is started by an operator such as a crew member.

In an embodiment shown in FIG. 4, the tank of the aircraft AC whose fuel characteristics are to be acquired corresponds to the central tank CT. These fuel characteristics comprise the density, the permittivity and the temperature of the fuel. During a selection step E1, the selection unit 10 detects and verifies whether the central tank CT contains fuel in sufficient quantity to fill the FPMU 5. If such is the case, the central tank CT is selected.

In another embodiment shown in FIG. 5, the selection unit 10 detects, during the selection step E1, whether one of the wing tanks WT1, WT2 contains fuel and if it contains sufficient fuel to fill the FPMU 5. In such a situation, one of the wing tanks WT1, WT2 is selected. The fuel characteristics of each of the wing tanks WT1, WT2 being identical, it suffices to acquire the fuel characteristics of one of the wing tanks WT1 in order to acquire those of the other wing tank WT2.

Once the tank CT, WT1, WT2 has been selected, a fuel circuit 3 is determined during a determination step E2 implemented by the determination unit 2. The fuel circuit 3 in one of the tanks, central tank CT, or wing tanks WT1, WT2 comprises a succession of pipes, the pump 4, the FPMU 5 and the valve 6A. The fuel circuit 3 can be arranged between two tanks CT, WT1, WT2. However, the ends 4A and 4B of the fuel circuit 3 are arranged in the tank CT, WT1, WT2, whose fuel characteristics are acquired. The pump 4 is arranged at the end 4A of the fuel circuit 3, the valve 6A is arranged at the opposite end 4B of the fuel circuit 3. The FPMU 5 is arranged between the pump 4 and the valve 6A.

During a bleed step E3 implemented by the bleed unit 11, the fuel circuit 3 is bled during a predetermined time, so as, in particular, to evacuate the air from the circuit 3 in the tank CT, WT1, WT2. The pump 4 is set to operate and injects from the end 4A the fuel present in the central tank CT (FIG. 4) or in the wing tank WT1, WT2 (FIG. 5) into the circuit 3. The valve 6A being open, the fuel circulates in the circuit 3 up to the end 4B of the circuit 3. The fuel exits the circuit 3 and returns to the tank CT, W1, WT2, having chased out the air present in the pipes of the circuit 3. At the end of the predetermined bleed time, it is estimated that the circuit 3 is bled and the valve 6A is closed.

During this filling step E4 implemented by the filling unit 7, the pump 4 continues to inject fuel into the circuit 3. The valve 6A is closed. This closure of the valve 6A blocks the fuel in the circuit 3 and the FPMU 5 fills with fuel.

The FPMU 5, once filled, measures values of the fuel characteristics. These values are acquired during an acquisition step E5 by an acquisition unit 15. The fuel characteristics comprise the density, the permittivity and the temperature of the fuel that fills the measurement unit 5. As shown in FIG. 3, the acquisition step E5 comprises a sub-step E51, during which the convergence module 14 acquires a succession of auxiliary values of each of the fuel characteristics. These auxiliary values are measured by the FPMU 5 then acquired by the convergence module 14 during a predetermined acquisition time. This acquisition time corresponds to the time at the end of which the measured auxiliary values converge towards stable acquisition values. As an example, the acquisition time is predetermined in an empirical manner. The acquisition values, stable over time, correspond to values of each of the fuel characteristics of the central tank CT (FIG. 4) or of the wing tank WT1, WT2 (FIG. 5).

The values of each of the fuel characteristics acquired are then translated into a signal representative of these fuel characteristics, which is transmitted, during a transmission step E6 implemented by the transmission unit 8, to a user device 9. As an example, the user device 9 corresponds to the crew instrument panel of the aircraft AC.

When the signals representative of the values of each of the fuel characteristics acquired by the acquisition unit 15 have been transmitted to the user device 9, the pump 4 stops pumping fuel into the circuit 3 and the valve 6A is open, during an emptying step E7 implemented by the emptying unit 12.

According to a variant, the circuit 3 furthermore includes a passive mechanical valve 13 arranged between the pump 4 and the FPMU 5, as shown in FIGS. 4 and 5. In the absence of pressure in the circuit 3 further to the pump 4 stopping pumping fuel, the mechanical valve 13 also opens. The fuel exits the circuit 3 through the end 4A of the pump 4 and through the end 4C of the mechanical valve 13.

According to a variant, the circuit 3 includes the valve 6B situated between the pump and the FPMU 5 and preferably upstream of the mechanical valve 13. When the pump 4 is running, the valve 6B is closed and when the pump 4 is stopped, the valve 6B is open.

In a particular embodiment, each of the tanks CT, WT1, WT2 comprises a FPMU 5, as each of the tanks CT, WT1, WT2 can be filled by a tanker independently of the other tanks CT, WT1, WT2.

Furthermore, it is possible to attribute the fuel characteristics values of one tank CT, WT1, WT2 to all of the tanks CT, WT1, WT2 if the fuel injected into the circuits 3 comes from the same source.

Furthermore, the operator can start the method for acquiring fuel characteristics further to a transfer of fuel from one tank CT, WT1, WT2 to another CT, WT1, WT2. The operator can also start the method for acquiring fuel characteristics when the default mode is displayed on one of the screens of the instrument panel.

The subject matter disclosed herein can be implemented in or with software in combination with hardware and/or firmware. For example, the subject matter described herein can be implemented in software executed by a processor or processing unit. In one exemplary implementation, the subject matter described herein can be implemented using a computer readable medium having stored thereon computer executable instructions that when executed by a processor of a computer control the computer to perform steps. Exemplary computer readable mediums suitable for implementing the subject matter described herein include non-transitory devices, such as disk memory devices, chip memory devices, programmable logic devices, and application specific integrated circuits. In addition, a computer readable medium that implements the subject matter described herein can be located on a single device or computing platform or can be distributed across multiple devices or computing platforms.

While at least one exemplary embodiment of the invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a", "an" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method for acquiring fuel characteristics on board an aircraft comprising a plurality of fuel tanks, the method comprising:
    a circuit determination step, implemented by a determination unit, comprising determining a fuel circuit in one fuel tank among the plurality of fuel tanks, wherein the fuel circuit circulates fuel and comprises at least one pump that pumps the fuel from the one fuel tank into the fuel circuit, a fuel properties measurement unit, and a first valve that opens and/or closes the fuel circuit;
    a filling step, implemented by a filling unit, comprising:
        filling the fuel circuit determined in the circuit determination step by pumping the fuel into the fuel circuit using the at least one pump until the fuel is inside the fuel properties measurement unit; and
        blocking the fuel in the fuel properties measurement unit by closing the first valve;
    an acquisition step, implemented by an acquisition unit, comprising acquiring a value, measured by the fuel properties measurement unit, respectively, for each of the fuel characteristics of the one fuel tank;
    a transmission step, implemented by a transmission unit, comprising transmitting, to a user device, a signal representative of the acquired values of the fuel characteristics; and
    an emptying step, implemented by an emptying unit after the transmission step, comprising stopping pumping the fuel into the fuel circuit through the at least one pump and emptying the fuel from the fuel circuit by opening a passive mechanical valve of the fuel circuit.

2. The method for acquiring fuel characteristics according to claim 1, wherein the fuel characteristics comprise at least:
    a density;
    a temperature; and
    a permittivity.

3. The method for acquiring fuel characteristics according to claim 1, comprising a selection step, implemented by a selection unit before the circuit determination step, comprising selecting one of the plurality of fuel tanks that contains fuel.

4. The method for acquiring fuel characteristics according to claim 1, comprising a bleed step, implemented by a bleed unit and occurring between the circuit determination step and the filling step, comprising controlling bleeding of the fuel circuit for a predetermined bleed time by opening the first valve.

5. The method for acquiring fuel characteristics according to claim 1, wherein the fuel circuit comprises at least a first end, a second end, and a third end, wherein the first end is positioned within the one fuel tank and is an inlet for the fuel circuit, wherein the second end is positioned within the one fuel tank and is an outlet for the fuel circuit, and wherein the third end is positioned within another fuel tank of the plurality of fuel tanks.

6. The method for acquiring fuel characteristics according to claim 1, wherein the acquisition step comprises a convergence sub-step, implemented by a convergence module, comprising acquiring a succession of auxiliary values of each fuel characteristic, which converge during a predetermined acquisition time to define an acquisition value of each fuel characteristic, wherein the succession of auxiliary values are measured during the predetermined acquisition time by the fuel properties measurement unit, and wherein the acquisition value of each fuel characteristic represents a value of each fuel characteristic transmitted to the user device.

7. A system for acquiring fuel characteristics on board an aircraft comprising a plurality of fuel tanks, the system comprising:
 a determination unit configured to determine a fuel circuit in one fuel tank among the plurality of fuel tanks, wherein the fuel circuit is configured to circulate fuel and comprises at least one pump configured to pump fuel from the one fuel tank into the fuel circuit, a fuel properties measurement unit, and a first valve configured to open and/or close the fuel circuit;
 a filling unit configured to:
  fill the fuel circuit determined by the determination unit by pumping, using the at least one pump, the fuel into the fuel circuit until the fuel is inside the fuel properties measurement unit; and
  block the fuel in the fuel properties measurement unit by closing the first valve;
 an acquisition unit configured to acquire a value, measured by the fuel properties measurement unit, respectively, for each of the fuel characteristics of the one fuel tank;
 a transmission unit configured to transmit, to a user device, a signal representative of the acquired values of the fuel characteristics; and
 an emptying unit configured to stop pumping the fuel into the fuel circuit through the at least one pump and to empty the fuel from the fuel circuit by opening a passive mechanical valve of the fuel circuit.

8. The system for acquiring fuel characteristics according to claim 7, comprising a selection unit configured to select one of the plurality of fuel tanks that contains fuel.

9. The system for acquiring fuel characteristics according to claim 7, comprising a bleed unit configured to control bleeding of the fuel circuit for a predetermined bleed time, by opening the first valve.

10. The system for acquiring fuel characteristics according to claim 7, wherein the fuel circuit comprises at least a first end, a second end, and a third end, wherein the first end is positioned within the one fuel tank and is an inlet for the fuel circuit, wherein the second end is positioned within the one fuel tank and is an outlet for the fuel circuit, and wherein the third end is positioned within another fuel tank of the plurality of fuel tanks.

11. The system for acquiring fuel characteristics according to claim 7, wherein the acquisition unit comprises a convergence module, configured to acquire a succession of auxiliary values of each fuel characteristic, which converge during a predetermined acquisition time to define an acquisition value of each fuel characteristic, wherein the succession of auxiliary values are measured during the predetermined acquisition time by the fuel properties measurement unit, and wherein the acquisition value of each fuel characteristic represents a value of each fuel characteristic transmitted to the user device.

12. An aircraft comprising a system for acquiring fuel characteristics according to claim 7.

* * * * *